(12) United States Patent
Vion et al.

(10) Patent No.: US 8,466,914 B2
(45) Date of Patent: Jun. 18, 2013

(54) X-RAY TOOL FOR 3D ULTRASOUND

(75) Inventors: Michael Vion, Lynnwood, WA (US); Allen David Snook, Snohomish, WA (US); Rohit Garg, Kirkland, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 780 days.

(21) Appl. No.: 12/663,088

(22) PCT Filed: Jun. 3, 2008

(86) PCT No.: PCT/IB2008/052166
§ 371 (c)(1),
(2), (4) Date: Dec. 4, 2009

(87) PCT Pub. No.: WO2008/149291
PCT Pub. Date: Dec. 11, 2008

(65) Prior Publication Data
US 2010/0188398 A1    Jul. 29, 2010

Related U.S. Application Data

(60) Provisional application No. 60/941,761, filed on Jun. 4, 2007.

(51) Int. Cl.
*G06T 15/00* (2011.01)
*G09G 5/02* (2006.01)

(52) U.S. Cl.
USPC ............................ 345/419; 345/426; 345/592

(58) Field of Classification Search
None
See application file for complete search history.

(56) References Cited

U.S. PATENT DOCUMENTS

| | | | |
|---|---|---|---|
| 6,254,540 B1 | 7/2001 | Kikuchi | |
| 6,633,305 B1 | 10/2003 | Sarfeld | |
| 6,803,931 B1 | 10/2004 | Roman | |
| 6,975,335 B2 | 12/2005 | Watanabe | |
| 2002/0183607 A1 | 12/2002 | Bauch | |
| 2005/0228250 A1* | 10/2005 | Bitter et al. | 600/407 |
| 2006/0111634 A1 | 5/2006 | Wu | |
| 2006/0203010 A1* | 9/2006 | Kirchner et al. | 345/629 |
| 2007/0046661 A1 | 3/2007 | Ma | |

FOREIGN PATENT DOCUMENTS

WO   2003045222 A2   6/2003

OTHER PUBLICATIONS

Hubbold, R.J. et al "Stereo Display of Nested 3D Volume Data using Automatic Tunnelling" Proceedings of the SPIE, vol. 3639, Jan. 1, 1999, pp. 200-207.
Viega, J. et al "3D Magic Lenses" UIST 1996, pp. 51-58.
Robb, R.A. "Visualization in Biomedical Computing" Parallel Computing, Dec. 1, 1999, vol. 25, No. 13-14, pp. 2067-2110.

* cited by examiner

*Primary Examiner* — Kee M Tung
*Assistant Examiner* — Leon T Cain, II

(57) ABSTRACT

A system and method is disclosed for rendering an ultrasound volume. An external image of an ultrasound volume is generated. A fractional part of the external image corresponds to a fractional portion of the ultrasound volume. A composite image of the ultrasound is generated using the external image, wherein the fractional part of the external image is replaced with an internal image of the ultrasound volume fractional portion. The internal image may be generated by changing a value of a visualization parameter used to generate the external image to a value more suitable for rendering an internal image. The ultrasound volume may include a organic structure, wherein the external image depicts an outer surface of the organic structure, and the internal image depicts a vascularity of the organic structure, such that the composite image simultaneously depicts both an outer surface and the vascularity of the organic structure.

13 Claims, 3 Drawing Sheets

X-RAY TOOL FOR 3D ULTRASOUND

The present disclosure is directed to systems and methods for displaying medical diagnostic images and, more particularly, to ultrasound data display systems/apparatus featuring interactive, user-controlled image manipulation.

Ultrasound technology is increasingly being utilized to beneficial effect in a wide variety of clinical applications. For example, two-dimensional (2D), three-dimensional (3D), and/or motion-reproduction (e.g., color and power Doppler velocities, loops/sequenced images, etc.) ultrasonic technology is now regularly used for collecting data and generating diagnostic images with respect to most bodily structures and volumes, including: abdominal (e.g., kidney, gallbladder), interventional (e.g., breast-ductal carcinoma/RFA contrast), obstetric/prenatal, breast (e.g., breast fibroadenoma), transcranial (e.g., cerebral artery), cardiac (myocardial ischemia), pediatrics/neonatal, musculoskeletal (e.g., biceps tendonitis), vascular (e.g., femoral vein thrombosis, pre-clinical atherosclerosis), and/or small parts (e.g., testicular abnormalities). As the demand on the part of doctors and their patients for ultrasound services and diagnostic data has increased, the market for related equipment has likewise grown. Modern embodiments of such equipment, such as the iU22, iE33, and HD11 XE Ultrasound Systems manufactured by Philips Electronic, can be enormously sophisticated tools for generating optimized image data containing high quality, undistorted acoustic information, often in real time, and commonly in large quantity.

Such ultrasound systems would be of little use, however, without complementary tools or systems (sometimes referred to as "quantification" tools or systems) designed and configured, for example, to receive and process such image data in an efficient and orderly fashion, and/or to store, distribute, and display such data at such times, and in such forms, as will be most convenient, useful and edifying to the intended viewer. Depending on the particular context, the intended viewer could be, for example, a technician tasked with using the ultrasound system to conduct a diagnostic test, a nurse or other health care worker processing or reviewing the test results, a physician attempting to develop a diagnosis based on such results, or a sick patient attempting to learn more about their medical condition.

One modern example of a solution for ultrasound data quantification is Philips Electronics' QLAB™ Advanced Quantification software product. The QLAB™ quantification software provides a user with the ability to analyze image data either on the ultrasound system itself, or on a separate personal computer or workstation (so-called 'off-cart' use). More particularly, Philips' QLAB™ features a user interface via which an operator is allowed, for example, to adjust one or more visualization settings associated with an ultrasound volume (e.g., brightness, transparency, thresholding, etc.). QLAB™ further features a sculpting tool and an eraser to enable an operator or practitioner to crop data from a visually-displayed ultrasound volume.

The patent literature includes additional teachings relative to user-adjustable display settings. For example, U.S. Pat. No. 6,975,335 to Watanabe discloses magnified or reduced areas of a display that are easily distinguished by shades of color and patent density corresponding to the magnification or reduction ratio of areas of the display. In addition, the Watanabe '335 patent describes a method for linking the displaying of a diagram to a pointing device so that a displayed portion is magnified when the area is pointed to by the pointing device.

U.S. Pat. No. 6,803,931 to Roman et al. discloses a graphical user interface (GUI) corresponding to an image display window through which a single image or a stream of images or video frames are displayed. According to the '931 Roman et al. patent, the GUI includes a zoom control box having an inner region positioned within an outer region, wherein the size of the inner region relative to the outer region represents the magnification of the portion of the image being displayed within the image display window. The magnification of the image being displayed can be increased or decreased, respectively, by positioning a cursor within the inner region and clicking a cursor control device, or by positioning the cursor outside of the inner region but inside of the outer region and clicking the cursor control device. As the magnification is increased or decreased, the size of the inner region relative to the outer region is changed accordingly. The portion of the image being displayed within the image display window is changed by clicking and dragging the inner region to the desired position within the outer region using the cursor control device.

In U.S. Pat. No. 6,633,305 to Sarfeld is disclosed an image editing system that uses a loupe cursor to magnify a selected area of a basic image displayed on a display device. According to the '305 Sarfeld patent, the system generates basic image data representing the selected area of the basic image, and generates magnified image data by magnifying the selected basic image data. It displays within the loupe cursor a loupe image based on the magnified image data. When a user editing signal is received for editing the loupe image, the system generates modified image data, and dynamically modifies the loupe image displayed within the loupe cursor based on the modified image data.

An ultrasound ultrasonic image scanning system for scanning an organic object is disclosed in U.S. Patent Application Publication No. 2006/0111634 by Wu that includes a display system for displaying a scanned image of the organic object in a plurality of display modes. According to the '634 Wu publication, the display system is operative to simultaneously display, as respective upper and lower images shown on a screen, a so-called 'zoom-out' image including a graphic border for defining a so-called zoom region of interest (ZROI) on the zoom-out image, and a so-called 'zoom-in' image containing a magnified version of such ZROI. The zoom-in updates in real time as the user uses a trackball to pan and/or resize the ZROI.

Despite efforts to date, a need remains for ultrasound data quantification solutions that are effective to distribute, display, and/or store acoustic information in such forms and at such times as to be convenient, useful, and/or informative to the intended recipients or viewers of such data. These and other needs are satisfied by the disclosed systems and methods, as will be apparent from the description which follows.

A system and method are disclosed for rendering an ultrasound volume including generating an external image of an ultrasound volume, wherein a fractional part of the external image corresponds to a fractional portion of the ultrasound volume, and generating a composite image of the ultrasound using the external image, wherein the fractional part of the external image is replaced with an internal image of the ultrasound volume corresponding to the fractional portion.

The internal image may be generated by changing a value of a visualization parameter used to generate the external image to a value more suitable for rendering an internal image. The ultrasound volume may include an organic structure, wherein the external image depicts an outer surface of the organic structure, and the internal image depicts a vascularity of the organic structure, such that the composite image simultaneously depicts both an outer surface and the vascularity of the organic structure.

Additional features, functions and benefits of the disclosed systems and methods for rendering an ultrasound volume will be apparent from the description which follows, particularly when read in conjunction with the appended figures.

To assist those of skill in the art in making and using the disclosed systems and methods for rendering an ultrasound volume, reference is made to the accompanying figures, wherein.

Figure 4:
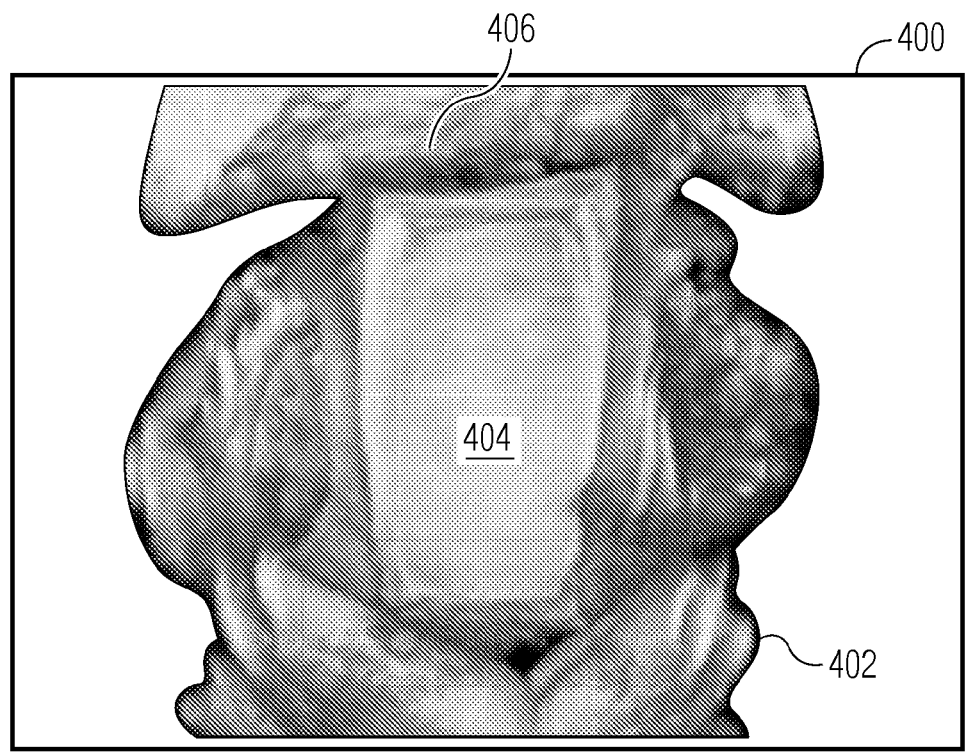
FIG. 4 illustrates a screen display of an external image of another ultrasound volume according to the present disclosure.
Figure 5:
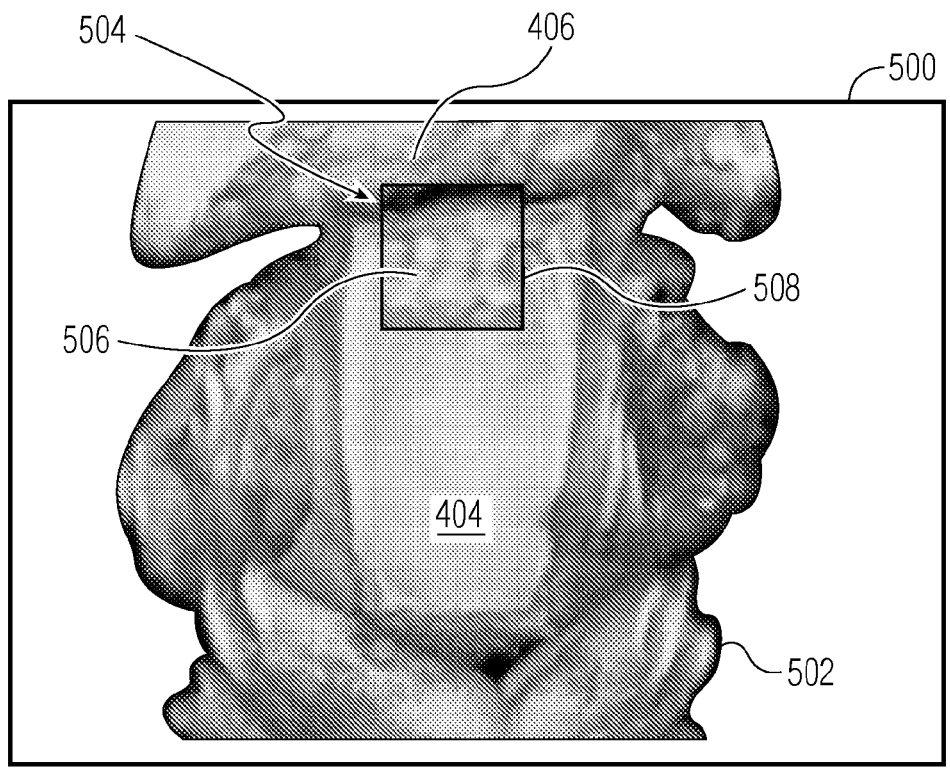
Figure 6:
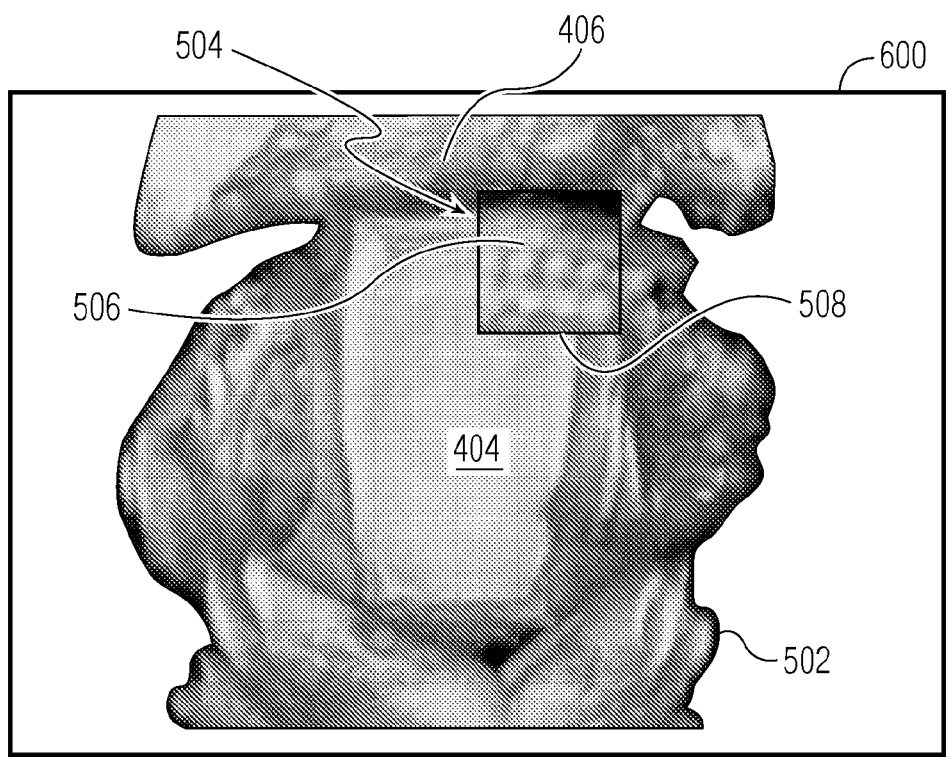

FIG. 5 illustrates a screen display of a composite image of the FIG. 4 ultrasound volume generated using the FIG. 4 external image, a part of the external image having been replaced with an internal image of the ultrasound volume according to the present disclosure; and FIG. 6 illustrates a screen display of a modified composite image of the FIG. 4 ultrasound volume, also generated using the FIG. 4 external image, showing a different portion of the ultrasound volume in internal view in response to a user-directed change according to the present disclosure.

In accordance with exemplary embodiments of the present disclosure, a 3D visualization tool is provided for rendering ultrasound volumes, wherein an external image of an ultrasound volume is generated, and a composite image of the ultrasound volume is generated using the external image. A fractional part of the external image corresponding to a fractional portion of the ultrasound volume may be replaced in the composite image with an internal image of the ultrasound volume corresponding to the same fractional portion of the ultrasound volume. Such functionality enables a user or viewer to obtain a localized view into the ultrasound volume without changing the overall visualization parameter values. In examples, a composite image of an ultrasound volume including an organic structure is provided including outer surfaces of much of the organic structure, as well as interior details associated with a selected portion of the organic structure.

Figure 1:
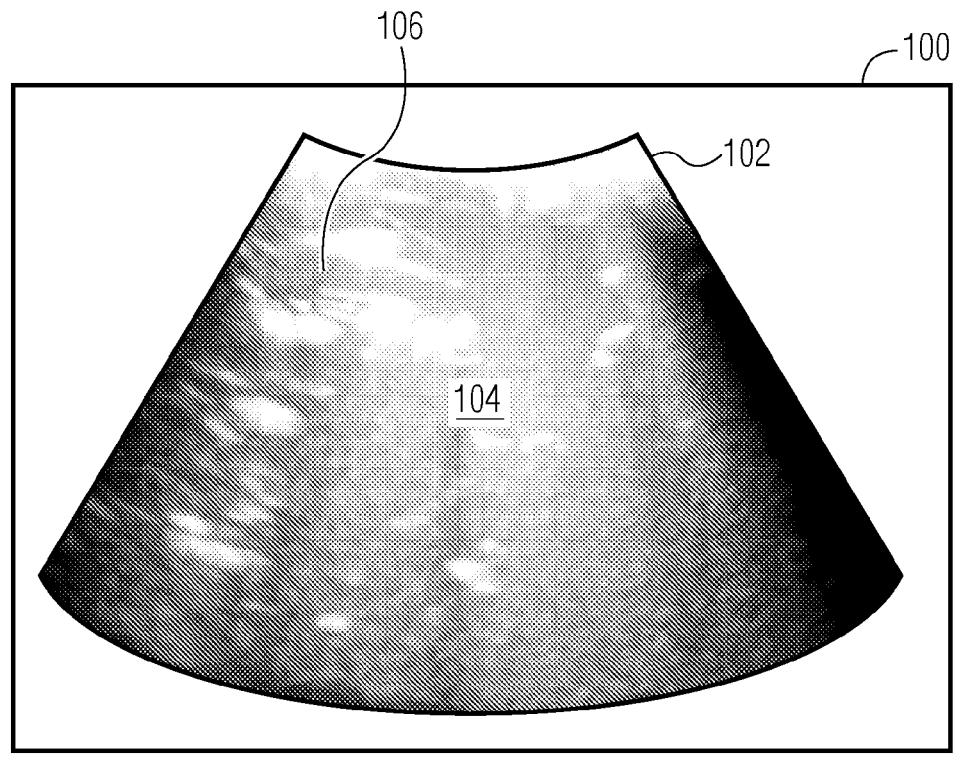
FIG. 1 illustrates a screen display of an external image of an ultrasound volume according to the present disclosure.

Referring now to FIG. 1, a screen image 100 associated with acoustic data from an ultrasound system (not separately shown) is displayed in accordance with an exemplary embodiment of the present disclosure. A portion of the screen image 100 includes an external image 102 of an ultrasound volume 104. The ultrasound volume 104 may contain an organic structure 106. An outer surface of the organic structure is at least partially shown in the external image 102.

The external image 102 may be generated by applying a set of visualization parameters to the ultrasound volume 104 for highlighting or emphasizing externally-oriented and/or externally-disposed aspects of the ultrasound volume 104 and/or the organic structure 106 contained therewithin. For example, such set of visualization parameters may include one or more of such visualization parameters as Brightness, Transparency, Thresholding, Lighting, Smoothing, Gray Map, Chroma Map, and Ray Cast Method. Other visualization parameters are possible.

Figure 2:
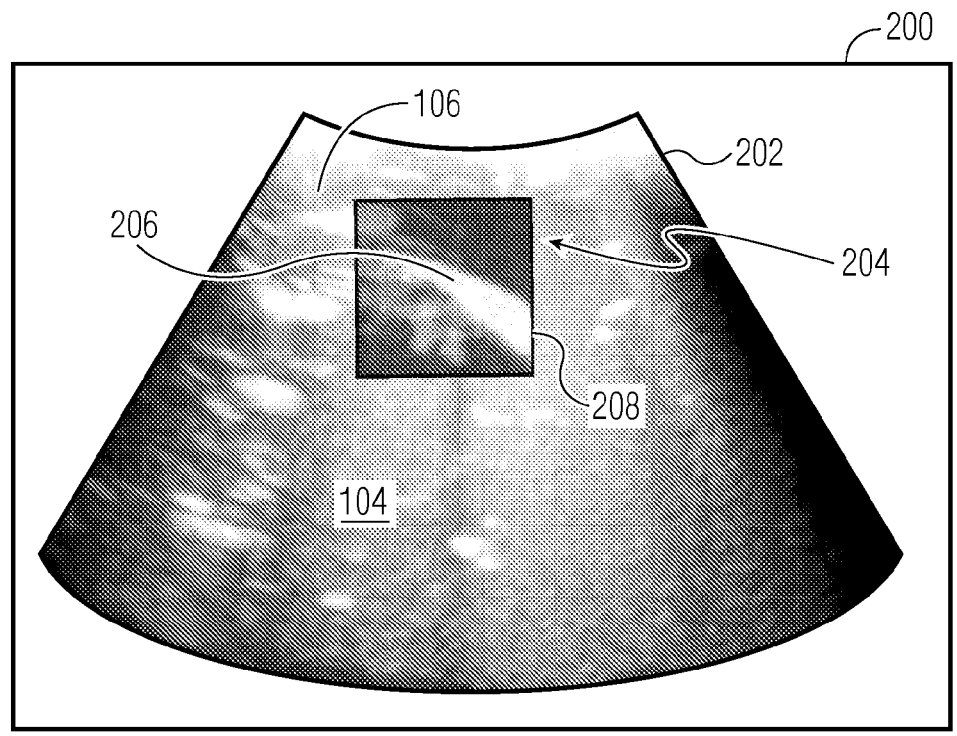
FIG. 2 illustrates a screen display of a composite image of the FIG. 1 ultrasound volume generated using the FIG. 1 external image, a part of the external image having been replaced with an internal image of the ultrasound volume according to the present disclosure.

Turning now to FIG. 2, a screen image 200 associated with acoustic data from an ultrasound system (not separately shown) is displayed in accordance with an exemplary embodiment of the present disclosure. A portion of the screen image 200 includes a composite image 202 of the ultrasound volume 104. The composite image may be generated using the external image 102 of FIG. 1, wherein a fractional part of the external image 102 is replaced with an internal image 204 of a corresponding fractional portion of the ultrasound volume 104. Within the internal view 204, a vasculature 206 of the organic structure 106 is shown. By contrast, the vasculature 206 of the organic structure 106 is not necessarily shown in the external image 102 of FIG. 1.

The fractional part of the FIG. 1 external image 102 replaced by the internal image 204 in FIG. 2 may be defined by a visible border 208, which may be depicted as part of the screen image 200. Alternatively, the screen image 200 may include no such border 208, or a differently-appearing border. For example, the border 208, shown in solid line in FIG. 2, may be shown in dashed or ghost line form, and/or may have another shape, e.g., depending on the shape of the internal image 204, which in turn may be of any suitable shape.

Other than within the internal image 204, the composite image 202 is typically generated by applying the visualization parameters and parameter values associated with the external image 102 of FIG. 1. Within the internal image 204, however, the composite image 202 is generated by applying different visualization parameters and/or parameter values than those associated with the external image 102. For example, a set of visualization parameters applied to the ultrasound volume 104 to generate the internal image 204 may include one or more of such visualization parameters as Brightness, Transparency, Thresholding, Lighting, Smoothing, Gray Map, Chroma Map, and Ray Cast Method, including a set of such visualization parameters similar to or identical to that used to generate the external image 102 of the ultrasound volume 104, wherein one or more of such visualization parameters in the case of the internal image 204 is associated with a different value than that associated with a corresponding visualization parameter in the case of the external image 102. Such differences may contribute to the generation of an internal (e.g., as opposed to an external) image of the ultrasound volume 104.

The values of the visualization parameters associated with the internal image 204 may be selected so as to highlight or emphasize internally-oriented and/or internally-disposed aspects of the ultrasound volume 104 and/or the organic structure 106 contained within the corresponding fractional portion of the ultrasound volume 104. Accordingly, within the internal image 204, the composite image 202 appears to at least some extent different than in a corresponding fractional part of the FIG. 1 external image 102 that is absent in FIG. 2. In accordance with the present disclosure, a value of a single visualization parameter associated with the internal image 204 that is at least incrementally different than the value of a corresponding visualization parameter associated with the external image 202 may be sufficient to generate and/or display a composite image (e.g., the composite image 202) of an ultrasound volume (e.g., the ultrasound volume 104) from an external image (e.g., the external image 102), wherein a fractional part of the external image is replaced by an internal image (e.g., the internal image 204) of the ultrasound volume. Other arrangements are possible, including wherein two or more common visualization parameters have different values, wherein one or more common visualization parameters have widely differing values, and/or wherein one or more visualization parameters applied to the ultrasound volume 104 to generate the internal image 204 or the external image 102 was not so applied to generate the other such view.

At least some of the visualization parameters applied to the ultrasound volume 104 to generate the internal image 204 can be the same or similar to those used to generate the external image 102. For example, the same parameter and parameter value may be used to generate either such image that does not necessarily correlate to suitability or non-suitability with respect to generating an internal image of a given ultrasound volume. In accordance with the present disclosure, such parameters may in some circumstances include Image Magnification.

The internal image 204 can be generated by applying parameters to the ultrasound volume 104 that are set in advance, and/or by default. Examples of such preset parameters and/or parameter values may include X-Ray, average, and minimum. Upon or after the composite image 202 being displayed to the viewer or user, he or she may elect to apply the same visualization parameters and/or parameter values to the entire ultrasound volume 104 that were applied to the fractional portion thereof to which the internal view 104 corresponds. In such circumstances, an internal image (not separately shown) of the ultrasound volume 104 may be generated that, in the context of the composite image 202, is substantially coextensive with, and therefore more or less fully replaces, the external image 102.

The above-discussed modifications or adjustments with respect to the visualization parameters and/or parameter values as between the internal image 204 and the external image 102 may be implemented in one or more of a plurality of different ways in accordance with embodiments of the present disclosure. For example, a computer mouse (not separately shown) (e.g., a rotatable wheel thereof, or a click-and-drag feature associated therewith), and/or any other suitable indicating, pointing, or cursor movement device (not separately shown) may be used to execute so-called "on-the-fly" modifications or adjustments to values associated with one or more such visualization parameters associated with the internal image 204 (e.g., changes to a Transparency visualization setting) to emphasize or highlight internally-disposed features within the corresponding fractional portion of the ultrasound volume 104. For another example, a group of different types of such modifications or adjustments, one or more of which may be determined in advance, and/or according to a pre-set menu or schedule of adjustments intended to create a particular visual effect or a distinct look (e.g., depending on the particular clinical application), may be implemented simultaneously, e.g., via a predetermined mouse click or series of mouse clicks, a particular software menu command (not separately shown), and/or a dedicated hardware switch (not separately shown). Other implementation techniques with respect to modifications or adjustments to the visualization parameters used to generate the internal image 204 are possible.

The internal image 204 (e.g., and/or the border 208 associated therewith) can be of a different size (e.g., of a larger or smaller absolute size than that shown in FIG. 2), and/or of a different size relative to that of the overall composite image 202, that of the screen image 200, and/or that of the external image 102, in accordance with embodiments of the present disclosure. In addition, the internal image 204 (and/or the border 208) may of a different shape than rectangular/square or polygonal (e.g., a curved and/or circular shape, an irregular shape, etc.), in accordance with embodiments of the present disclosure. For example, a computer mouse (not separately shown) (e.g., a rotatable wheel thereof, or a click-and-drag feature associated therewith), and/or any other suitable indicating, pointing, or cursor movement device may be used to execute so-called "on-the-fly" modifications or adjustments to the size or shape of the internal image 204 (and/or of the border 208). For another example, the size and/or shape of the internal image 204 (and/or of the border 208) may be changed to, from, or between any one of a number of predetermined sizes or shapes, including to, from, or between one or more customized shapes corresponding that of a particular organic structure or volume (e.g., as viewed from a particular perspective or vantage point) or a separately identifiable portion thereof, e.g., via a predetermined mouse click or series of mouse clicks, a particular software menu command (not separately shown), and/or a dedicated hardware switch (not separately shown). Other implementation techniques with respect to modifications or adjustments to the size and/or shape of the internal image 204 (and/or of the border 208) are possible.

The above-discussed modifications or adjustments to the visualization settings of the external image 102 of the ultrasound volume 104 can be implemented to cause the composite image 202 to reflect one or more desired visual effects or distinct looks within the internal image 204 (e.g., as compared to those of the ultrasound volume 104 as a whole) in accordance with embodiments of the present disclosure. For example, in some embodiments in accordance with the present disclosure, visualization settings applied to the ultrasound volume 104 to generate the external image 102 can be selected so as (and/or generally tend) to afford the ultrasound volume 104 an opaque and/or three-dimensional overall appearance, such that the external image 102 will appear to show an outer surface or wall(s) of a particular organic structure (e.g., a heart or other bodily organ). In at least some such instances, modifications or adjustments to such visualization settings can be selected so as to produce within the internal image 204 a visual effect (e.g., akin to an X-ray effect) for viewing one or more structures (e.g., cardiac vascularity, such as a coronary artery) and/or functions (e.g., valve operation, blood flow, etc.) ordinarily understood and/or expected by a practitioner or technician to be disposed (or to take place) within the ultrasound volume 104, rather than on its periphery or outer surface. In other words, the compound visualization parameters applied to the ultrasound volume 104 may be determined or selected to give the internal image 204 (and/or the border 208) the appearance of a 'window' with respect to the inner structural and/or functional constituents of an organic structure contained within the ultrasound volume 104, while at the same time, and in the same image, at least some portion of the external or outer wall structures of such organic structure is also visible (e.g., in those portions of the composite image 202 appearing outside the internal image 204). Applying compound visualization settings to the ultrasound volume 104 in such a way can be advantageous, at least insofar as it can provide a practitioner or technician with important and powerful visual cues and/or contextual information with respect to the external (e.g., outer wall) structure of a bodily structure in the same image in which he or she may also (e.g., simultaneously) observe important structural and/or functional details associated with interior regions of such bodily structure.

As discussed above, in accordance with embodiments of the present disclosure, the image magnification or zoom parameters associated with the external image 102 of the ultrasound volume 104 may be maintained and/or kept constant, even as other visualization settings are modified or adjusted to generate the internal image 204 thereof. For example, in accordance with embodiments of the present disclosure, applying the same magnification or zoom settings to the ultrasound volume 104 both within and outside the fractional portion thereof associated with the internal image 204 can be advantageous, insofar as such an arrangement may tend to increase and/or maximize the amount of accurate (e.g., clinically useable and/or reliable) visual or image information appearing at or near the border 208. In other words, to the extent compound visualization parameters are applied to the ultrasound volume 104 to produce the appearance of a 'window' to the inner workings of an otherwise externally-rendered bodily structure, such window can be sharply defined (e.g., the window can appear to be relatively sharply 'cut' from surrounding external structure) so as to reduce and/or minimize any loss of visual detail associated with rendering such inner workings.

In accordance with embodiments of the present disclosure, the ultrasound volume 104 to which the above-discussed external, internal, and/or compound set of visualization parameters are applied can be any one or more of the following ultrasound volume types: an echo volume, a color volume, and/or an echo+color volume. Still further ultrasound volume types are possible.

Figure 3:
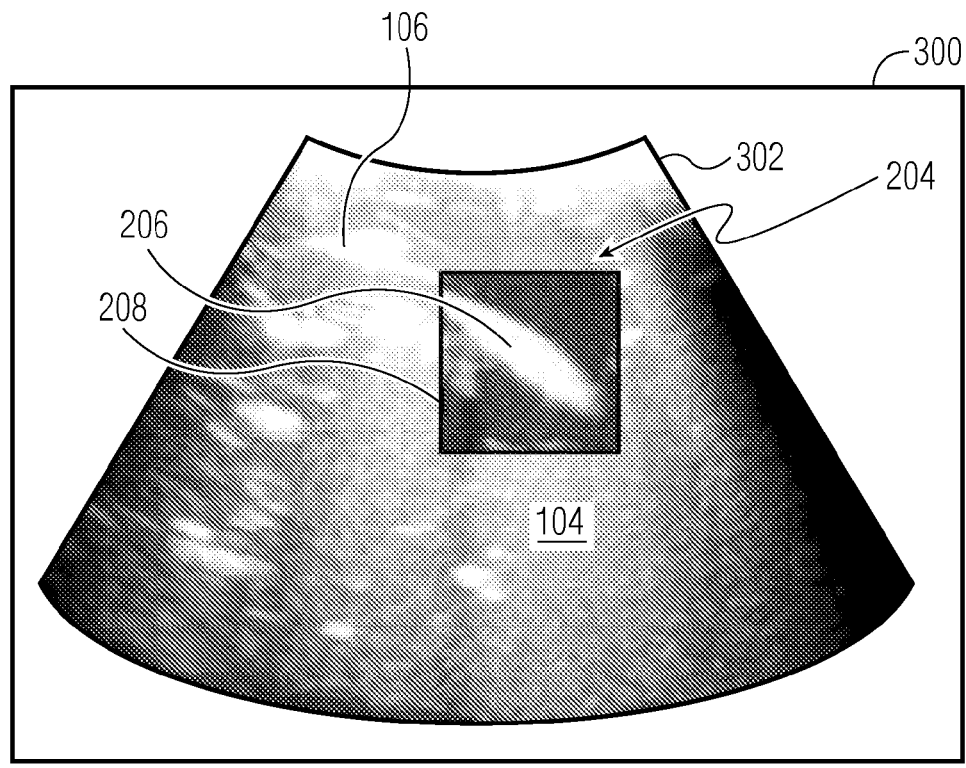
FIG. 3 illustrates a screen display of a modified composite image of the FIG. 1 ultrasound volume, also generated using the FIG. 1 external image, showing a different portion of the ultrasound volume in internal view in response to a user-directed change according to the present disclosure.

Referring now to FIGS. 2 and 3, a position of the internal image 204 (and/or of the border 208) within the screen image 200, and/or within the composite image 202, may be changed in accordance with the present invention to correspond to a different fractional portion of the ultrasound volume 104, and/or to another fractional part of the FIG. 1 external image 102. For example, a computer mouse (not separately shown) (e.g., a rotatable wheel thereof, or a click-and-drag feature associated therewith), and/or any other suitable indicating, pointing, or cursor movement device may be used to so move the internal image 204 (and/or the border 208) from the position within the screen image 200 or within the composite image 202 shown in FIG. 2 to a new position, e.g., as shown in FIG. 3 with respect to a new screen image 300, and in a new composite image 302. Other techniques for so moving the interior image 204 (and/or the border 208) are possible.

In accordance with embodiments of the present disclosure, and as shown in FIGS. 2 and 3, upon the internal image 204 (and/or the border 208) being moved as described immediately above to correspond to the new fractional portion of the ultrasound volume 104, the same visualization parameters and/or parameter values discussed above and associated with generating an internal image may be applied to the ultrasound volume 104 there, where previously, the visualization parameters and/or parameter values associated with generating an external image were applied. By the same token, and/or by virtue of the internal image 204 (and/or the border 208) being moved away from one fractional part of the external image 102 and to a new fractional part thereof, the same visualization parameters and/or parameter values discussed above and associated with generating an external image may now be applied to the corresponding fractional portion of ultrasound volume 104, thereby restoring to the now new composite image 302 the previously replaced fractional part of the external image 102. To the extent the new position of the internal image 204 within the composite image 302 is sufficiently close to the earlier position therein, some overlap may exist as between the previous and new corresponding fractional parts of the external image 202. In such circumstances, the previously replaced fractional part of the external image 102 may only be partly restored by virtue of such movement of the internal image 204.

Referring now to FIG. 4, a screen image 400 associated with acoustic data from an ultrasound system (not separately shown) is displayed in accordance with an exemplary embodiment of the present disclosure. A portion of the screen image 400 includes an external image 402 of another ultrasound volume 404. The ultrasound volume 404 may contain an organic structure 406. An outer surface of the organic structure is at least partially shown in the external image 402.

As discussed above, the external image 402 may be generated by applying a set of visualization parameters to the ultrasound volume 404 for highlighting or emphasizing externally-oriented and/or externally-disposed aspects of the ultrasound volume 404 and/or the organic structure 406 contained therewithin.

Turning now to FIG. 5, a screen image 500 associated with acoustic data from an ultrasound system (not separately shown) is displayed in accordance with an exemplary embodiment of the present disclosure. A portion of the screen image 500 includes a composite image 502 of the ultrasound volume 404. The composite image may be generated using the external image 402 of FIG. 4, wherein a fractional part of the external image 402 is replaced with an internal image 504 of a corresponding fractional portion of the ultrasound volume 404. Within the internal image 504, a vasculature 506 of the organic structure 406 is shown. By contrast. the same vasculature 506 of the organic structure 406 may not be shown, or at least may not be as effectively shown, or as easily visible, in the external image 402 of FIG. 4.

Referring now to FIGS. 5 and 6, a position of the internal image 504 (and/or of the border 508) within the screen image 500, and/or within the composite image 502, may be changed in accordance with the present invention to correspond to a different fractional portion of the ultrasound volume 404, and/or to another fractional part of the FIG. 4 external image 402. For example, a computer mouse (not separately shown) (e.g., a rotatable wheel thereof, or a click-and-drag feature associated therewith), and/or any other suitable indicating, pointing, or cursor movement device may be used to so move the internal image 504 (and/or the border 508) from the position within the screen image 500 or within the composite image 502 shown in FIG. 5 to a new position, e.g., as shown in FIG. 6 with respect to a new screen image 600, and in a new composite image 602. Other techniques for so moving the interior image 504 (and/or the border 508) are possible.

Embodiments of the present disclosure include a computer system (not shown, e.g., including a processor, related accessories such as a computer mouse and/or a trackball, and a computer monitor or other display) and a related algorithm or software product operable via such computer system and/or by said processor for permitting a user of such computer system to display the screen images 100, 200, 300, 400, 500, and 500 including the various images depicted therein of the respective ultrasound volumes 104, 404, and to manipulate such images in the manner described herein, including but not limited to achieving the above-described 'window' or 'X-ray' visual effect. For example, hardware-related embodiments of the present disclosure may include a personal computer or workstation, including a computer display or monitor, e.g., such as are presently used to run and/or utilize the above-discussed Philips Electronics QLAB™ Advanced Quantification software product off-cart, or a computer-implemented ultrasound system (e.g., on-cart) such as the above-discussed Philips Electronics iU22, iE33, and/or HD11 XE Ultrasound Systems. Software-related embodiments of the present disclosure may include a quantification software product including all relevant features and aspects of the above-discussed Philips Electronics QLAB™ software product, with additional code, for example, and/or one or more appropriate software 'plug-ins' for implementing additional features and aspects as disclosed herein. Embodiments of the present disclosure may further include a computer-readable medium including a computer-executable algorithm for implementing the ultrasound imaging features and functions disclosed herein. For example, such an algorithm may include appropriate computer-executable code.

The systems and methods of the present disclosure are particularly useful for displaying and manipulating displayed images of ultrasound volumes. However, the disclosed systems and methods are susceptible to many variations and alternative applications, without departing from the spirit or scope of the present disclosure.

The invention claimed is:

1. A method for rendering an ultrasound volume, the method comprising:
   generating an image of an ultrasound volume, the image showing an outer surface of the volume image as opaque;
   placing an internal image window at a position over the volume image, the internal image window being defined by a border and a transparency visualization parameter which causes the surface within the border to be displayed transparently so that an internal image of the internal structure of the volume is displayed in anatomical alignment with a fractional part of the volume over which the internal image window is placed; and
   moving the internal image window with a user control to a new position over the volume image, wherein the fractional part within the border at the new position is replaced with an internal image of the volume in anatomical alignment with the new position of the internal image window,
   wherein the outer surface of the volume image outside of the border is displayed as opaque at both positions.

2. A method for rendering an ultrasound volume according to claim 1, wherein the image generation step includes setting a transparency visualization parameter to reflect an opaque parameter value and applying the visualization parameter to the ultrasound volume, and further comprising generating the internal image by setting said the transparency visualization parameter to a second parameter value different than the first parameter value, the second parameter value being at least incrementally more suitable than the first parameter value for purposes of rendering the surface over an internal image of the ultrasound volume as transparent.

3. A method for rendering an ultrasound volume according to claim 2, the method further comprising displaying a composite image of the ultrasound volume with an internal image window on a screen of a computer monitor in conjunction with a pointing device, and permitting a viewer of the computer monitor screen to use the pointing device to selectably incrementally adjust a value of the transparency visualization parameter associated with the internal image.

4. A method for rendering an ultrasound volume according to claim 2, further comprising using the user control to set at least a further visualization parameter selected from the group comprising Brightness, Transparency, Thresholding, Lighting, Smoothing, Gray Map, Chroma Map, and Ray Cast Method.

5. A method for rendering an ultrasound volume according to claim 4, wherein the further visualization parameter is an intensity parameter, the second value of the transparency visualization parameter is preset to include at least one selected from the group comprising X-ray, average, and minimum.

6. A method for rendering an ultrasound volume according to claim 1, wherein an image magnification parameter associated with the internal and external images is of substantially the same value.

7. A method for rendering an ultrasound volume according to claim 1, wherein the ultrasound volume is one selected from a group comprising an echo volume, a color volume, or an echo+color volume.

8. A method for rendering an ultrasound volume according to claim 1, wherein the ultrasound volume includes an organic structure, the ultrasound volume image depicts an outer surface of the organic structure, and the internal image depicts a vascularity of the organic structure, such that a composite image of the two images simultaneously depicts both an outer surface of the organic structure and the internal vascularity thereof.

9. A method for rendering an ultrasound volume according to claim 1, the method further comprising displaying the ultrasound volume image on a screen of a computer monitor in conjunction with a user-movable cursor, and permitting a viewer of the computer monitor to place an internal image window by using the cursor to designate a fractional part of the ultrasound volume for internal viewing.

10. A method for rendering an ultrasound volume according to claim 1, the method further comprising displaying a composite image of the ultrasound volume and internal image window on a screen of a computer monitor, and upon receipt of an appropriate command from a viewer of the computer monitor screen, selectably entirely replacing the composite image with an internal image of the ultrasound volume, and associated with the same visualization parameters and parameter values of the internal image of the fractional part.

11. A method for rendering an ultrasound volume according to claim 1, the method further comprising displaying a composite image of the ultrasound volume and internal image window on a screen of a computer monitor in conjunction with a user movable cursor positioned over the composite image, and permitting a viewer of the computer monitor to reposition the internal image window to a new position by moving the cursor to the new position over the composite image.

12. A method for rendering an ultrasound volume according to claim 1, wherein a respective second fractional part of the ultrasound volume image corresponds to a second fractional portion of the ultrasound volume, and the method further comprising modifying a composite image of the ultrasound volume and internal image window to form a modified composite image wherein the second fractional part is replaced with a second internal image window of the ultrasound volume corresponding to the second fractional portion.

13. A method for rendering an ultrasound volume according to claim 12, the method further comprising displaying a composite image of the ultrasound volume and internal image window on a screen of a computer monitor in conjunction with a user movable cursor, and permitting a viewer of the computer monitor screen to repo the second internal image window to a new position by using the cursor to designate the second fractional portion of the ultrasound volume for internal viewing.

* * * * *